United States Patent [19]
Marcus

[11] Patent Number: 6,032,156
[45] Date of Patent: Feb. 29, 2000

[54] SYSTEM FOR AUTOMATED GENERATION OF MEDIA

[76] Inventor: Dwight Marcus, 779 Cedar Point Pl., Westlake Village, Calif. 91362

[21] Appl. No.: 09/053,597

[22] Filed: Apr. 1, 1998

Related U.S. Application Data

[60] Provisional application No. 60/042,564, Apr. 1, 1997.

[51] Int. Cl.[7] ................................................. G06F 17/30
[52] U.S. Cl. .............................. 707/104; 707/2; 707/8; 707/102; 707/103; 707/104; 345/302; 345/328
[58] Field of Search .................................. 707/1, 2, 7, 8, 707/201, 202, 100, 102, 103, 104; 395/200.35; 706/50, 59; 345/328, 337, 339

[56] References Cited

U.S. PATENT DOCUMENTS

| | | | |
|---|---|---|---|
| 4,290,141 | 9/1981 | Anderson et al. | 455/2 |
| 4,377,870 | 3/1983 | Anderson et al. | 455/2 |
| 4,566,030 | 1/1986 | Nickerson et al. | 379/92.04 |
| 5,041,972 | 8/1991 | Frost | 705/10 |
| 5,109,482 | 4/1992 | Bohrman | 345/328 |
| 5,206,929 | 4/1993 | Langford et al. | 345/328 |
| 5,227,863 | 7/1993 | Bilbrey et al. | 348/578 |
| 5,307,456 | 4/1994 | MacKay | 345/328 |
| 5,353,391 | 10/1994 | Cohen et al. | 345/435 |
| 5,388,197 | 2/1995 | Rayner | 345/328 |
| 5,414,808 | 5/1995 | Williams | 345/328 |
| 5,428,774 | 6/1995 | Takahashi et al. | 707/101 |
| 5,440,730 | 8/1995 | Elmasri et al. | 707/203 |
| 5,483,276 | 1/1996 | Brooks et al. | 348/2 |
| 5,515,490 | 5/1996 | Buchanan et al. | 345/328 |
| 5,519,828 | 5/1996 | Rayner | 345/328 |
| 5,550,965 | 8/1996 | Gabbe et al. | 345/328 |
| 5,634,020 | 5/1997 | Norton | 345/339 |
| 5,644,686 | 7/1997 | Hekmatpour | 706/45 |

(List continued on next page.)

OTHER PUBLICATIONS

Lee, Taekyong, "Query Processing Technique for Multimedia Presentation Graphs", Eighth International Workshop on Reasearch Issues In Data Engineering, 1998. "Continuous–Media Databases and Applications". Feb. 23–24, 1998 pp. 130–138.

Piamsa–nga, Punpiti, "A Parallel Model for Multimedia Database on Cluster System Environment", IEEE International Symposium on Industrial Electronics Proceedings, 1998. ISIE '98. Jul. 7–10, 1998, pp 648–652 vol. 2.

Wu, Chao–Hui, "Querying multimedia presentations", Proceedings IEEE Conference on Protocols for Multimedia Systems–Multimedia Networking, Nov. 24–27, 1997 pp 64–73.

*Primary Examiner*—Anton W. Fetting
*Assistant Examiner*—Shahid Alam
*Attorney, Agent, or Firm*—Duane, Morris & Heckscher LLP

[57] ABSTRACT

A system and method for creating audiovisual programming has media elements, such as audiovisual clips, stored in a library. A database contains selected information about each of the media elements. The stored information in the database does not dictate the temporal sequence of the media elements. Media elements are selected in response to a request for media programming, and arranged in a temporal organization. A user does not select the individual media elements or their temporal organization. Transitions between audiovisual clips are determined by the system based on information stored in the database and predetermined preferences as to types of transitions. Transition information includes a variety of possible transition points in an individual clip, capable of selection by the system. Separate transitions for the audio and video portions of audiovisual clips may be provided. For unique media programming, a unique sequence of cues may be included within the program for use in verification of viewing and comprehension. Upon completion of the selection of the media elements, the sequence, and the transitions, the media elements are assembled into a media program, such as a video tape.

41 Claims, 7 Drawing Sheets

U.S. PATENT DOCUMENTS

| | | | |
|---|---|---|---|
| 5,659,793 | 8/1997 | Escobar et al. | 345/302 |
| 5,680,639 | 10/1997 | Milne et al. | 707/104 |
| 5,687,331 | 11/1997 | Volk et al. | 345/337 |
| 5,689,641 | 11/1997 | Ludwig et al. | 395/200.02 |
| 5,713,021 | 1/1998 | Kondo et al. | 707/104 |
| 5,721,815 | 2/1998 | Ottesen et al. | 395/200.09 |
| 5,721,878 | 2/1998 | Ottesen et al. | 395/500 |
| 5,729,471 | 3/1998 | Jain et al. | 364/514 A |
| 5,748,187 | 5/1998 | Kim et al. | 345/302 |
| 5,748,956 | 5/1998 | Lafer et al. | 707/104 |
| 5,751,883 | 5/1998 | Ottesen et al. | 386/27 |
| 5,752,029 | 5/1998 | Wissner | 707/104 |
| 5,754,851 | 5/1998 | Wissner | 707/104 |
| 5,765,164 | 6/1998 | Prasad et al. | 707/104 |
| 5,799,150 | 8/1998 | Hamilton et al. | 395/200.33 |
| 5,819,286 | 10/1998 | Yang et al. | 707/104 |
| 5,826,102 | 10/1998 | Escobar et al. | 345/302 |
| 5,852,435 | 12/1998 | Vigneaux et al. | 345/302 |
| 5,861,880 | 1/1999 | Shimizu et al. | 345/302 |

SYSTEM FOR AUTOMATED GENERATION OF MEDIA

RELATED APPLICATIONS

This application claims priority from U.S. Provisional Patent Application No. 60/042,564, filed Apr. 1, 1997, which is hereby incorporated by reference in its entirety.

FIEKD OF THE INVENTION

This invention relates to a method and computer-implemented system for creation of audiovisual programming.

BACKGROUND OF THE INVENTION

There have been recent substantial advances in the capacity to design customized audio visual programs for specific purposes from a library of existing video clips and audio elements. Customization of audiovisual programing is useful in many applications. For example, in advertising certain products, and in particular automobiles, one promotional technique is to prepare promotional videotapes which are sent to potential customers on their request. The desirability of customizing such videotapes to demographic or other characteristics of individual consumers are of course substantial. Health care practitioners and managed care entities have begun to provide instructional videotapes to patients with information regarding managing of various diseases and conditions. Customizing of such information to the disease and condition of the individual, and demographic characteristics of the individual, such as age, income, educational level, psychographic characteristics such as perceived wellness and willingness to change behaviors, and other factors, would be valuable for increasing the effectiveness of such video tapes in communicating the information to the recipient.

In accordance with present technology, it is possible to create and store a library of brief video clips, and provide a database of information regarding these clips. However, in accordance with the present technology, a human editor must make the ultimate selection of individual clips, and provide the final editing decisions, creation and selection of transitions so that there is a smooth visual and audio transition between adjoining clips in the program, and checking of the content of the clips to determine that there is proper coverage of the appropriate subject matter in an appropriate sequence. Automating of this editing process would make possible substantial flexibility and new possibilities for creation of audiovisual programming.

Once videotapes have been provided to the user, it is difficult to verify whether or not the user has viewed the program. Even if the program has been viewed, the level of comprehension is difficult to assess.

It is accordingly an advantage of this invention that the disadvantages of the prior art may be overcome.

Additional advantages of the invention, and objects of the invention, will become apparent from the detailed description of a preferred embodiment which follows.

SUMMARY OF THE INVENTION

According to a first aspect of the invention, a system and method of creating media programming are provided. A database is provided which contains selected information about each of a large number of media elements. The media elements may be, for example, audiovisual clips. The elements themselves are maintained in a suitable library. The method provides for selecting some of those media elements in response to a request for media programming, and selecting a temporal organization for the media elements. However, the temporal organization is not dictated by the selected information that regarding each of the media elements. The system selects and orders the media elements according to the data in the request, and according to information, such as permitted transitions, regarding the media elements. The system prevents a user from selecting individual media elements. The media elements are then assembled into media programming.

In another aspect of the invention, a method is provided for verifying viewing and comprehension of a unique media program. The method includes providing, in the unique media program, a unique sequence of cues. The method includes receiving from a viewer of the unique media program information relative to said cues, such as responses to questions included on a questionnaire, or in response to a telephone call made by the viewer. The received information is then compared to the sequence of cues to determine whether or not the program was viewed, and the level of comprehension by the viewer.

In another aspect of the invention, a method of creating audiovisual programming from stored audiovisual media elements is provided. In a first step, from a database containing information concerning the audiovisual media elements, certain audiovisual media elements are selected. A temporal sequence for the selected elements is designated. Transitions between the media elements are automatically selected.

DETAILED DESCRIPTION OF A PREFERRED EMBODIMENT

Figure 1:
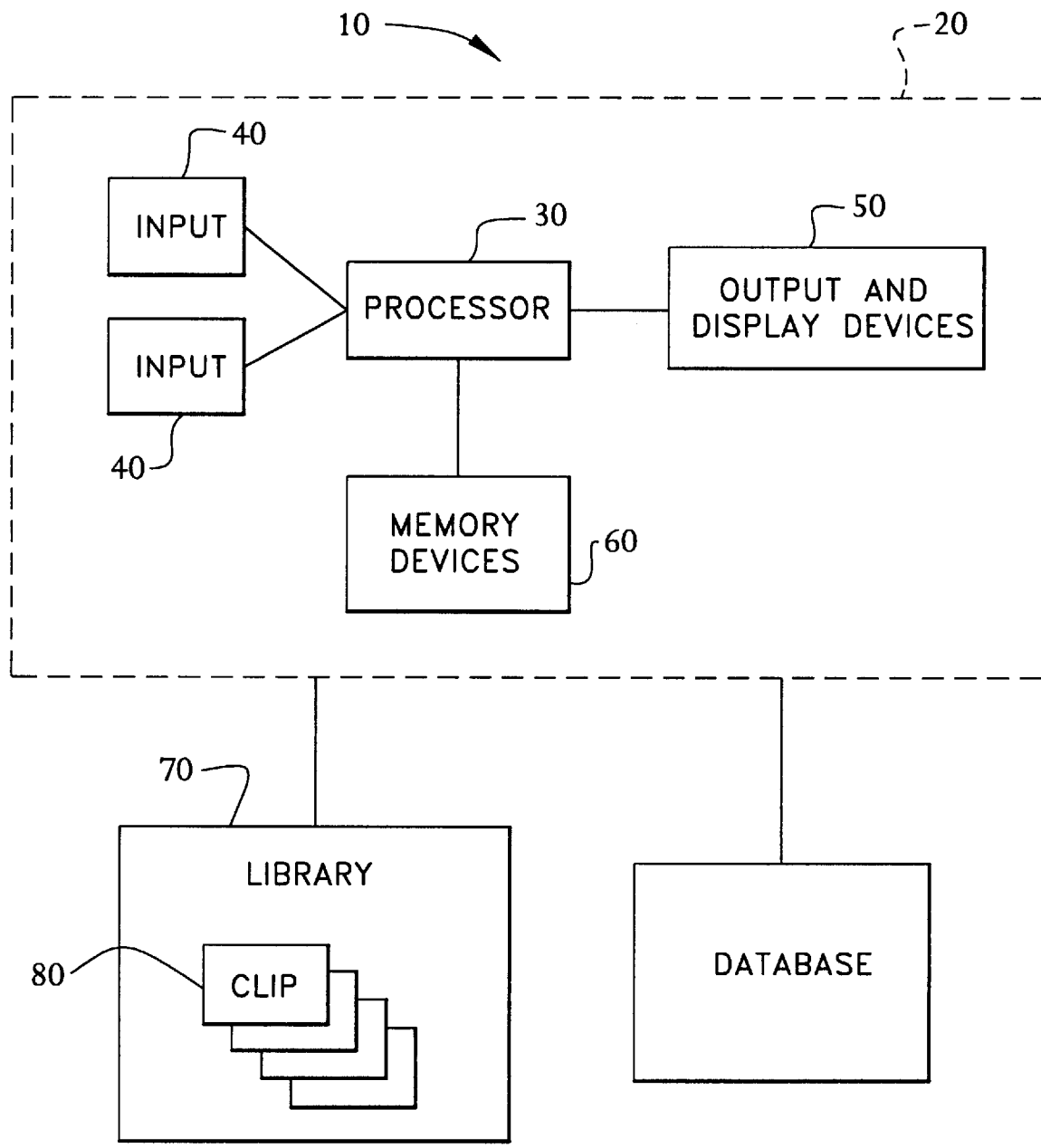
FIG. 1 is a schematic diagram of a system according to the invention.

Referring to FIG. 1, there is depicted a system 10 according to the invention. System 10 includes a computer 20 including processor 30, input devices 40, output and display devices 50 and memory devices 60. Computer 20 may be a conventional personal computer with suitable processor speed and memory capacity and speed. Computer 20 communicates in a suitable manner with library 70 of audiovisual clips 80. Library 70 may be stored on any suitable storage medium of adequate bandwidth and retrieval time characteristics. At present, certain fixed or hard disk systems provide superior performance to other options. Digitized audiovisual clips 80 are stored in library 70. Each audiovisual clip is suitably identified, such as by the name of one or more files which make up the clip.

Database.

Figure 2:
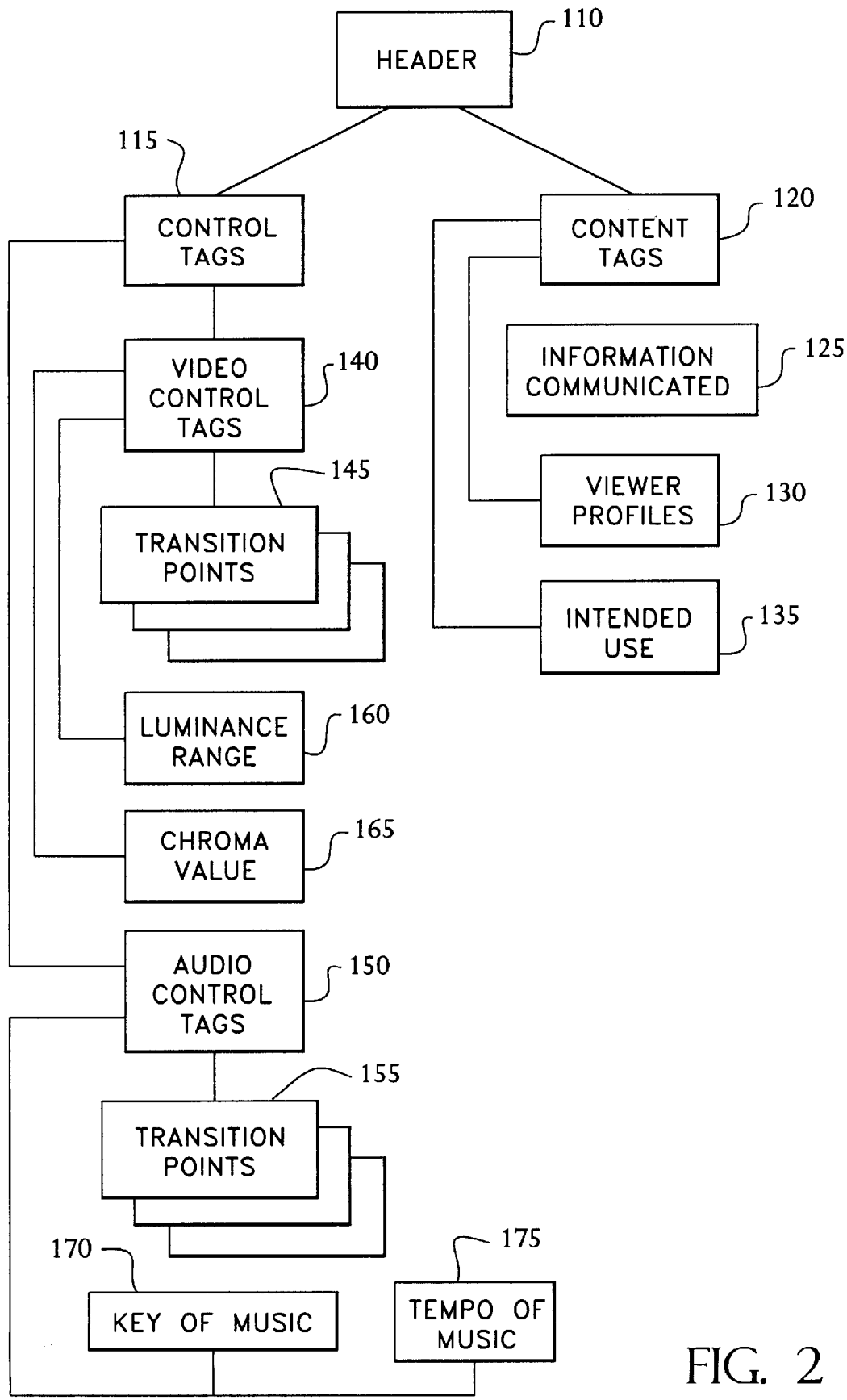
FIG. 2 is a schematic diagram indicating information contained in a database according to the invention.

Computer 20 is also suitably associated with a database 100. Database 100 contains unique identifying information for each clip and has associated therewith additional information often arranged in a hierarchical manner. Referring to FIG. 2, this information will be referred to herein as a header 110. Individual items of information within the header will be referred to herein as tags. The tags are divided into two general categories, namely control tags 115 and content tags 120. Content tags 120 contain information identifying the content of the clip. The content is often embodied in three general categories, namely content, i.e., information communicated by the clip, as indicated by block 125, viewer profiles for viewers most likely to be receptive to the clip, indicated by block 130, and intended use of the clip, indicated by block 135. The content tags contain information defined by a suitable system of classification of information. For example, in a database of clips for the assembly of video programs concerning medical information, the content information may, in addition to other systems, such as for categories of content mentioned above, make use of International Classification of Disease codes. In databases directed to assembly of programs for other topics, other coding systems are used for the content information. Fields may be provided to indicate technical complexity, specific items of information conveyed, demographic characteristics of actors in clips, style of script, and other suitable information. One or more fields may be provided within the content tag to define content. The system by which the content information is defined is preferably organized to provide for relationships among types of information. Such relationships may be levels of generality, and other subject matter relationships.

Figure 3:
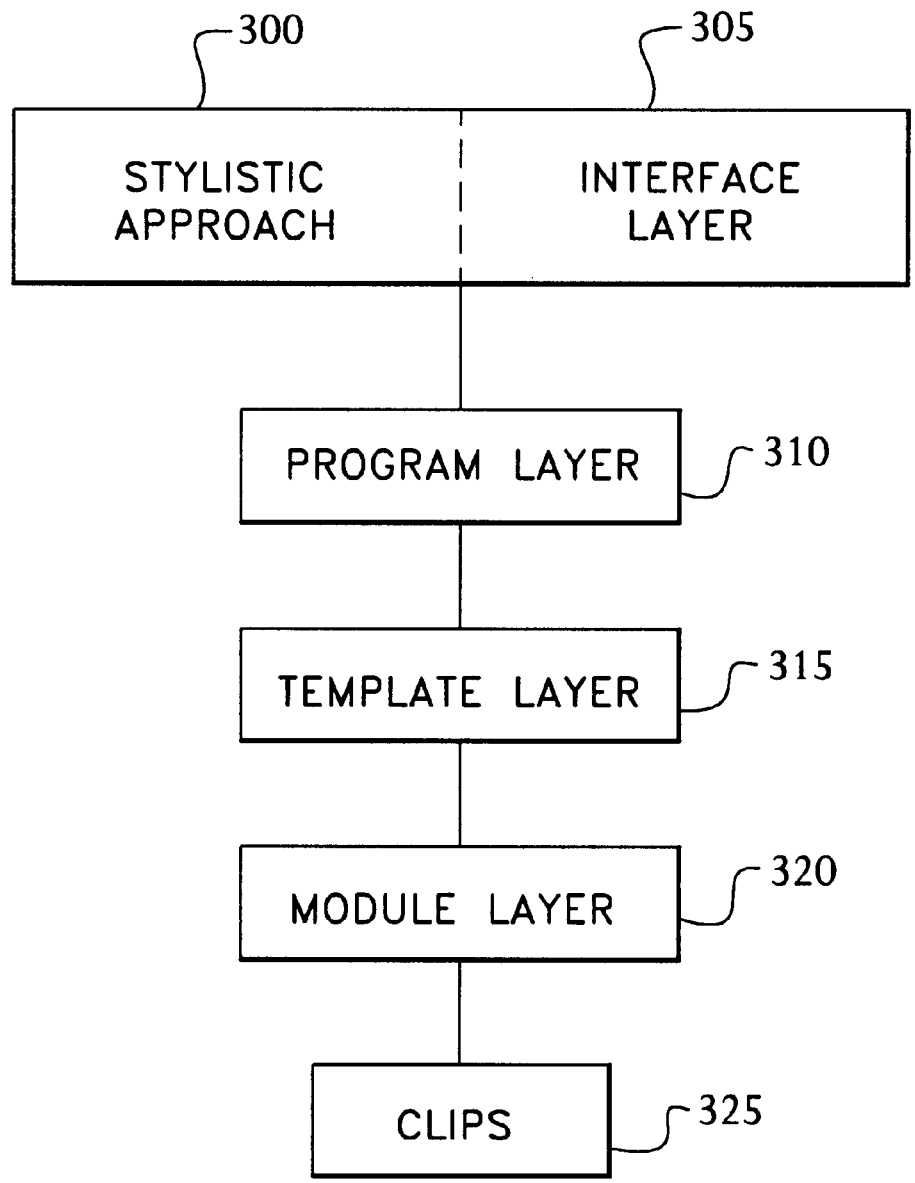
FIG. 3 is a schematic diagram indicating the organization of a database according to the invention.

The organizational structure of the database may be hierarchical, with each layer of hierarchy defining a specific set of organizational principles. Referring to FIG. 3, at the highest level the global behavior of the universe of elements is defined. This is equivalent to automating a 'look-and-feel' function for the entire unit of programming. A given stylistic approach 300 can be defined through the use of default values which will be employed, for example, in the treatment of transitions between adjacent clips. There may be defined a set or range of transition values, such as a range from hard-cut to 24-frame dissolve. In this example, the master look-and-feel level of organization might define hard-cut as the aesthetically optimal, and therefore the default, choice. Numerous other aesthetic or programmatic choices that affect the delivery and placement of media elements in the concatenated stream can be defined.

Also at the highest level of organization, typically used in on-line applications only, there may be provided the viewer/user interface options which define the ways in which any given class and security level of user will be allowed to actively as well as passively interact with media assets. We will call this the INTERFACE LAYER 305. At this level of organization, the behaviors of ancillary assets such as promotional segments, information identifying the system, advertisements and news-flashes are defined. These assets embody aesthetic, program or instructional design, as well as market-driven, or viewer defined behaviors.

Immediately below this layer is preferably the meta-content layer. This is called the PROGRAM LAYER 310. Here are defined the type of assets and the core content descriptions of those assets. By way of example, the types of assets may be defined as training, informational, and entertainment assets. Examples of core subject matter would be "medical", at the highest level, "health management", at a lower level, and "diabetes mellitus", at a still lower level.

Next in the hierarchy is the instructional design layer, or TEMPLATE LAYER 315. This layer is characterized by a family of defining values which describe the range of the target audience in specific demographic and psychographic terms. Additionally, the overall outline of the subject matter is contained in this layer and is associated with demography where appropriate. These outlining functions are secondary, however, to the temporal organizational templates embodied in this layer. Here the instructional designer, or interactive author, defines the preferred temporal modes of presentation of the universe of assets. For example, the instructional designer might define that the block of programming content called EFFECTS ON THE HEART is presented across three fundamental age groups, two levels of detail (summary/cursory and in-depth), both gender specific groups and four distinct ethnicity components. Within this multi-dimensional array of program assets, the instructional designer might also define that the material be presented in the preferred sequence of—INTRODUCTION TO THE HEART, IMPACT OF DIABETES ON THE CARDIOVASCULAR-VASCULAR STRUCTURES, EFFECTS OF DIET, EFFECTS OF EXERCISE, Q&A SESSION, SUMMARY.

Below the instructional design layer are the smaller organizational elements which allow for elasticity in the specifics of the implementation of the temporal design. This is called the MODULE LAYER 320 and in special instances the SEQUENCE LAYER. Fundamental to this layer are weighting factors which control likelihood of asset use, and allow for the deployment of elements which are free to float temporally in order to accomplish certain transitions and effective deployment of those elements which are slave to the temporality functions. These elements as a group are shorter sequentially-patterned program elements of content which organize under the temporality principles of the higher layer. The free floating elements may have various linking geometries or parameters at the opening and closing thereof. Such elements can be used to bridge elements that cannot themselves be linked because a direct link is either disallowed or would involve use of disfavored transitions.

The lowest level of organization is that of the individual media elements or assets themselves. This is called the CLIP LAYER 325. These elements carry tags which define their specific content, such as: DIABETIC HEART, LEFT VENTRICLE, DAMAGE TO, HYPERGLYCEMIA, MALE, AGE 50, TALKING HEAD. The first three content tags will be noted as being in hierarchical order from most general to most specific. The next two are examples of demographic tags, and the final tag is a simple example of a tag denoting style. These elements also carry production-specific control tags, which, as discussed in more detail below, define such characteristics as allowable exit/entrance transitions for both audio and video.

It is important to note that, in the operation of the system, there is an inhibition layer between the clip and the searching mechanism. The inhibition layer assures that the system does not include in the programming every clip that is responsive to a query provided by a user. The inhibition mechanism may be responsive to psychographic characteristics of the user, such as age, level of education, or even reason for the query. The tags are responsive to this type of information. The inhibition mechanism may be modified dynamically as the database is mined for suitable assets. The inhibition mechanism may be viewed as in a multi-dimensional set of psychographic requirements. Clips can be evaluated for their responsiveness in the various dimensions. The system may set, or the user may select, a length of time for the program, and the inhibition mechanism will operate to limit the total number of clips selected to the selected time, as well as choosing clips according to suitability for the viewer and the viewer's purpose.

Referring again to FIG. 2, control tags define audio and video components of clips. The audio and video information may be entirely separate as indicated by block 140, VIDEO CONTROL TAGS, and block 150, AUDIO CONTROL TAGS. For example, a minimum number of control tags would be, for each of audio and video, transition points 145, 155 an optimum transition point from the beginning of the clip, a first possible transition point from the beginning of the clip, a last possible transition point from the beginning of the clip, an optimum transition point from the end of the clip, a last possible transition point from the end of the clip, and a first possible transition point from the end of the clip. Each of these points may be defined in time, by video frames, by tags of clips that may be the subject of the transition, or by content parameters. These points may be defined by human post-production editors entering such information into the database in response to suitable prompts contained in the software. These points may also be defined by truth-table or expert-system defaults, which may or may not reference either video or audio content. The variable beginning and exit points may be referred to as creating fuzzy extremities on the clips. This is believed to be a novel feature as compared to existing databases of audiovisual assets, and lends significant flexibility to the process of creation of transitions. Numerous optional control tags can be used, such as, with reference to video information, a luminance range 160 for the opening and closing of the clip, preferred or required transitions, including length and type of transition, a dominant chroma value for each of the opening and closing of the clip, start and end points for dialog and action. With reference to audio information, control tags may include key of music 170, tempo of music 175, preferred transitions and other information. This type of information can be derived by suitable software reviewing the data stream before or after the clips are concatenated, or in advance of the assembly process using clip analogs or proxies containing suitable information from the tags.

Creation of Database.

The database is created by identifying each clip or other asset and defining values of the control tags and content tags for each. Values of the various control tags and content tags may be defined by a user, either during development of the script for the clip or upon completion of the clip. For example, the program may include screens prompting a user to select a value for each control tag from a menu of options. Different screens may be provided for different users, such as dialog editors, audio editors, and video editors, to enter values for appropriate control and content tags. Alternatively, values of various tags may be created automatically by truth tables or decision-capture systems, or other automated techniques, either with or without human assistance. Such systems may act from information derived from analysis of existing clips using image-recognition software, from analysis of scripts entered into text, or from other information provided by human editors.

Figure 4:
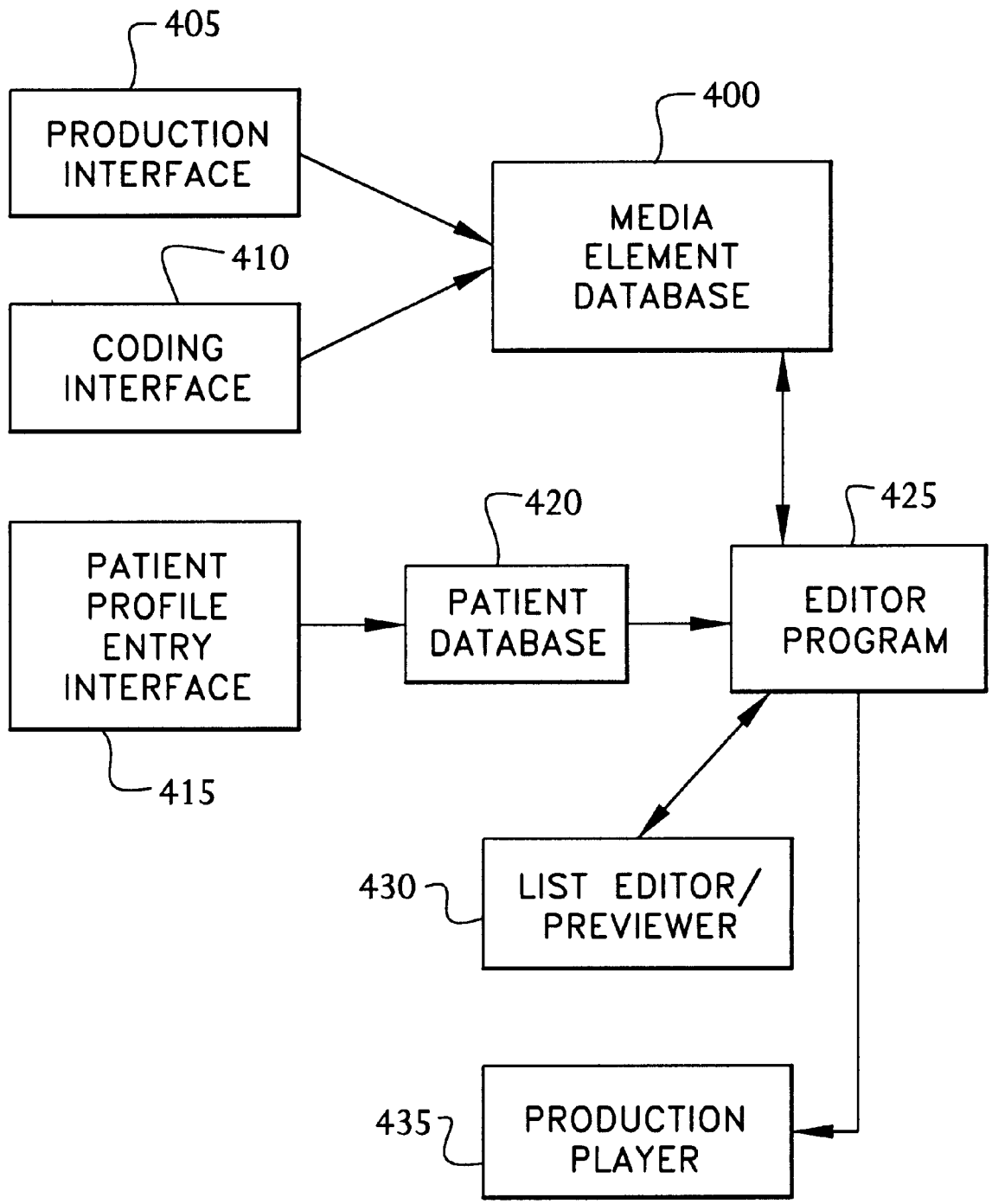
FIG. 4 is a schematic diagram indicating software elements in the system according to the invention.

By way of example only, a system for creation of a database for use in connection with creation of medical programming will now be described with reference to FIG. 4. The system may include five primary components, each of which will be provided with its own user interface:

1. A production interface 405 which provides an interactive means of importing a video clip into the system and recording the transition production information.
2. A coding interface 410 to allow the entry of the medical and patient selection codes which apply to the clip.
3. A patient profile entry interface 415 and decision list processor.
4. A decision/transition list editor 430 with built-in transition previewer for both audio and video components of clips.
5. A production player/recorder which embodies an engine for both audio and video transitions.

Each of the foregoing components operates as an independent entity in the exemplary system. Each component is started by the user selecting an icon from an appropriate folder. The user interface is preferably be graphical in nature. Actual keyed data entry is preferably kept to a minimum where most entries are made by selecting an option from a set or an entry from a list.

The Production Interface

The production interface 405 is the interface designed to provide a structured, interactive means of importing a video clip into the system. A standard container, such as OMF, may be utilized as a standardized vehicle for the transmission of the proprietary tags. When selected, the user will be presented with a screen containing fields for the entry of the following:

Clip ID—This will become the primary key or file name.

Source—Where the clip will be read from. Options may include DAT tape or network.

The user will also be presented with one or more interfaces to enter the audio/video transition fields and the coding (medical/patient demographic) information. Before being allowed to exit the process, defaults will be applied to the transition fields not specified by the user. The user may be required to preview the clip just imported.

The Coding Interface

The coding interface 440 is the GUI designed to perform the entry of the medical and socio-demographic selection codes which apply to the clip. These include the ICDs for which this clip is applicable, the socio-demographic and medical attributes of those patients assumed to be the most likely potential viewers of the clip, and any special fields which when present in the client/patient profile will cause this clip to be selected. All fields may be selected from preestablished lists or groups displayed as "radio-buttons". As the ICD set may require the designation of hundreds or thousands of codes, a suitable method of use of the hierarchical nature of the ICD structure may be utilized to simplify the selection process. These may be selected during the script outlining or scripting process by the use of menus or existing fields incorporated in the scripting software.

The Patient Profile Entry Interface

The Patient profile entry interface 415 is the GUI designed to perform the entry of the general, medical and socio-demographic codes for the specific patient for which the product is to be produced. The general section may require the most data entry including patient name, address, social security number, insurance billing numbers, referring entity identification and any text which is to be added to the final video. Systems, such as those used in the health care industry, may be employed to extract relevant information from existing patient records. In the case of on-line use, the medical and socio-demographic sections will be "click to select" entry similar in nature to the entry process performed by the coder when the clip is imported. The result of this process will be to create an entry in the patient database 420. The information is then forwarded to the editor program 425.

Based on the topic requested, such as a condition which the patient has been diagnosed with, and the demographic information, editor program 425 will, as discussed below, produce a recommended decision list, or preliminary edit decision list (EDL) file for further processing. Subsequently, the final EDL is created in an evolutionary manner. At first, a sample order of clips, without transitions, is analyzed. The order and identities of the clips is then revised. When the order and identities of the clips has been finalized, the transitions are computed. The transitions are then executed and inserted into the stream by use of a system of removal of portions of the tag extremities used in temporal transitions.

The List Editor/Previewer

The List Editor/Previewer 430 is the GUI designed to provide the production editor with the ability to change, add to and preview the EDL that has been produced by the editor program 425 in response to information entered in the Patient Profile Entry Interface 415.

The Production Player

Each clip, clip component, or other media asset, is stored in three distinct segments:

1. lead-in segment
2. main body
3. exit segment

Transitions can only be performed on the lead-in and out segments. The production player 435 is launched with the name of the patient EDL to be played. The EDL will be analyzed and each transition rendition time estimated. The production player will then process each command in the EDL. Most commands, which require very little processing, cause a more detailed command to be written to the player FIFO which controls the player output thread. Other process intensive commands, such as a transition, will be rendered, stored to disc and the detailed command with its disc location is added to the player FIFO. As each EDL command is processed, the remaining estimated time flow is modified until the program determines that future transition rendering will be able to be completed before the player output thread requires it. At this point, the player output thread will be started taking its input instructions from the player FIFO. The player output thread will operate asynchronously, transferring each data component specified in the player FIFO to the appropriate hardware component, such as video and audio decoder modules, text merge processor, etc., whose output drives the device for recording the program, such as a videotape deck.

Upon completion, the required managerial and billing information will be generated and stored in an appropriate database.

The transition process will require the identification of both an exit and lead-in point, and a transition function specification. This pair of fields are refined into a single recommended field as defined above, and then the final recommended EDL is obtained. These fields are contained in the preliminary EDL which is being played. The appropriate time positions are located in both the exit and lead-in segments. The first frame of each segment is decoded into separate buffers and then the transition function is applied to each matching pixel of both images to produce the third rendered frame buffer. A similar process is also applied to the matching audio sample points associated with the currently rendered frame. The video and audio is then re-compressed and written to the output transition file.

Values of certain control and content tags, such as key or tempo of music, may be determined by suitable software from the clip.

It is to be emphasized that the foregoing system is merely exemplary, and does not limit the scope of systems that may be implemented within the scope of the inventions described in this application.

Editor Program.

Programs are created from clips by an editor program.

Figure 5:
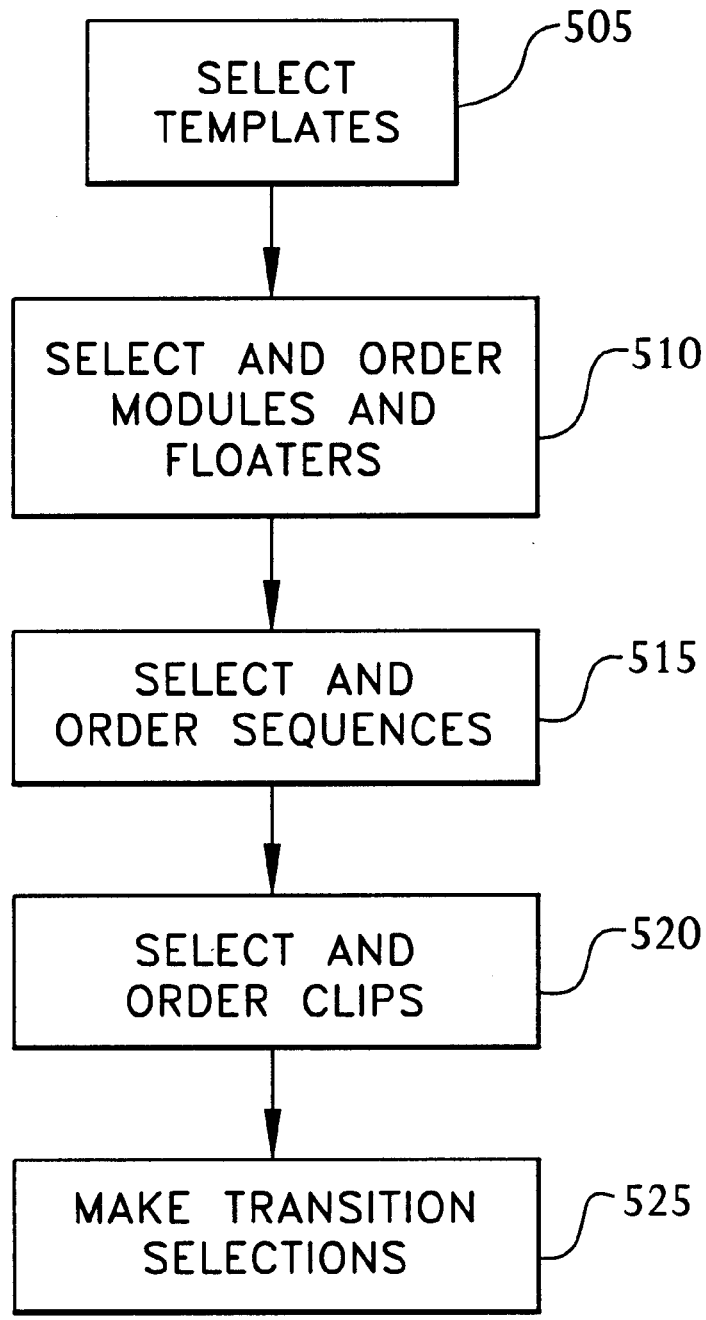
FIG. 5 is a flow chart showing steps in the assembly of an edit decision list in the method according to the invention.

The identify and order of the clips that comprise a program may be defined by a variety of methods varying in the degree of control exercised by the individual user. At the level of least control by the user, the user defines only the overall functional requirements for the program. For example, in the assembly of programs for education of patients about health issues, the user may define only the demographic characteristics of the intended recipient of the program and the information to be conveyed, e.g., management of a particular condition. In one embodiment, the system may simply select appropriate clips from the database and apply suitable transitions. Alternatively, an expert system included within the editor program selects and orders one or more suitable templates as shown in block 505 of FIG. 5. The template may incorporate the demographic characteristics and information to be conveyed, or may contain only sequential requirements for the underlying structures used in the program. Using the requirements in the selected templates and the demographic characteristics and other requirements specific to the program, as well as the inherent structural characteristics of the modules and sequences, the expert system or truth table then selects and orders one or more suitable modules and floater sequences, as shown by block 510 of FIG. 5. Using the requirements in the selected modules and the inherent structural characteristics of sequences, the expert system or truth table selects and orders suitable sequences, as shown by block 515 of FIG. 5. Finally, using the requirements in the selected sequences and the inherent structural characteristics of the clips, the expert system or truth table selects and orders suitable clips, as shown by block 520 of FIG. 5. The expert system or truth table also makes transition selections at the beginning and end of the audio and video portions of each clip, as shown by block 525 of FIG. 5. At any level in this process, if there is an incompatibility, the expert system or truth table may discard an element and replace it with a substitute element, or employ suitable transition methods. For example, if it is not possible to assemble acceptable sequences in the manner dictated by the modules under the template, the expert system or truth table may discard one or more modules and select alternatives that meet the requirements of the template.

The tags may include information regarding such attributes as luminance, chrominance, music tempo and key, and colors, at the beginning and end of each clip. Alternatively, a MIDI record of the audio portion of the clip may be analyzed. The editor program may apply expert system software or truth tables to determine whether a direct transition between any two clips meets aesthetic requirements. If not, the system may identify a suitable type of transition for both clips, add a bridge between the clips, or determine that one of the clips must be discarded. For example, if the keys of the music in two adjacent clips are incompatible, the system may add a bridge consisting of a burst of percussion in the audio portion of the program.

The viewer or user may directly select templates, modules, or sequences, depending on the degree of control desired. Decisions regarding either specific production decisions or global stylistic choices or content or order can be captured by the system by, in addition to expert systems, truth-table or other decision tree programming specific decision collection fields provided to content developers. Expert systems, truth tables and other systems may be used to create the tags associated with the clips.

Use of expert systems, or decision-capture systems is of interest because the system might organically evolve stylistic tendencies which might mimic or mirror those of creative professionals. Templates might be provided to content providers or even to end-users, which would allow a specific style of editing, audio cutting or mixing, or program formation; perhaps a template may be provided associated with an individual editor. Such decision-capture systems already exist for other uses which could be adapted to the assembly of audio and video.

In one embodiment, the user creates queries depending on the qualities desired for the organization levels to be identified. The editor program then identifies suitable templates, modules or sequences based on the queries. The relative importance of different items in the queries may be weighted. The weighting may be supplied by the user in response to suitable prompts, or may be generated automatically by the system based on existing programming. Using suitable relationships among data items, the user may be presented by the editor program with one or more templates, modules or sequences that represent a fundamental response, another set that represent a secondary response, a third set that represent a tertiary response, and so forth.

Assembly Program.

Figure 6:
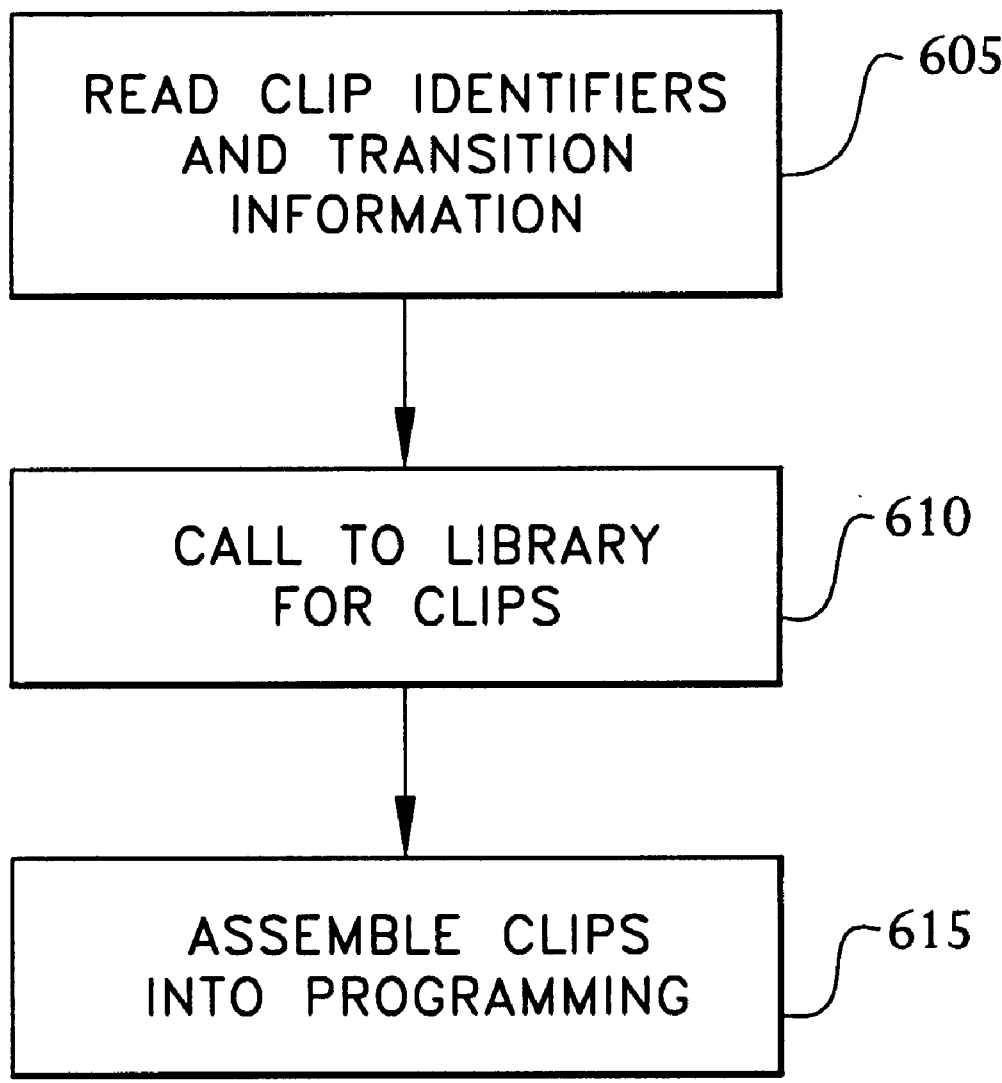
FIG. 6 is a flow chart showing steps in the assembly of programming in a method according to the invention.

Once the set of clips has been defined, the assembly of the clips from the library takes place. This is accomplished by an assembly program. Referring to FIG. 6, the assembly program reads a file of clip identifiers and transition information created by the editor program as shown by block 605, and calls to the library for each identified clip as shown by block 610. The identified clips are then transmitted from the library to a suitable destination. The assembly program uses the transition information in assembling the clips into the program. If the clips are transmitted to a suitable digital to analog converter, the clips may be assembled into a program on videotape without compression. However, in order to assemble the program as a digital audiovisual program in memory, or to transmit the program over telephone lines or the Internet, data compression is required. Suitable data compression techniques and standards may be used.

The assembly program may also dictate particular transitions. For example, asymmetrical transitions in audio are advantageous. A leading edge audio transition which is exponential and short, and a trailing edge transition in audio which is linear and long is preferred. The video transitions need not match the audio transitions.

The following is a technique which is believed by the inventor to be suitable for improving performance of compression of the programming, for use in compression formats, of which MPEG is an example, which achieve performance using predictive compression which includes both forward and backward looking frames. The technique is the elimination of the complex frames from the MPEG stream using the last-in and first-out video marker tags to determine the amount of leading and trailing video which might, in a worst-case scenario, participate in a visual effect. By eliminating these (P and B) frames, it is possible to employ a partial decoding of the (Huffman) algorithm, rather than a full decode/encode cycle. Additionally, the elimination of these PB frames allows impunity in the concatenation points employed. This freedom is bought at the price of increased bandwidth requirements, but only for small segments of video rather than entire clips.

Another technique is applicable to compression formats, such as MPEG, where the chrominance data is subsidiary to the luminance data. This technique involves emulating the MPEG transitions by extracting luminance-only data. Because the chrominance data 'rides on' the luminance, this can still be employed to generate useable dissolves. Using this technique, the full decode process can be further reduced, and thus accelerated, by processing this luminance in averaged blocks of pixels. These pixel blocks are employed in the encode process. Even without the use of MPEG, it is possible that some or all of these shortcuts might be effectively employed to accelerate the creation of dissolves without use of a full decode/recode cycle.

Viewer Database.

Separately from the database of media assets described above, there may be provided a database of viewer information. This database defines the identity of each viewer, including name and address information, and may also include social, economic and medical data regarding the viewer, the history of items viewed by the viewer, and a file of preference information for the viewer. In an on-line environment, the viewer may be prompted to provide viewer identification information which may be entered into a database or may be retained temporarily as a viewer data record for use in creation of customized programming.

Verification of Viewing.

The verification of viewing of the delivered video program is difficult to accomplish. It is important for the well-being of the viewer when the program contains therapeutic or training video programming, and useful for all content to assess the effectiveness of delivering information via customized video programming. An effective system would: (a) allow the distributor of the programming to know if no effort had been made on the part of recipient to watch the delivered material; (b) provide disincentives for fast-forwarding and skipping through the program; (c) allow for the confidential verification of the particular program watched, thus allow for the confidential generation of viewer-comprehension testing; (d) provide incentives, perhaps monetary or material, for the successful viewing of the material; (e) maintain confidentiality of the viewer and/or of the precise content of the delivered program. The following viewing verification system performs all of the objectives outlined above.

Figure 7:
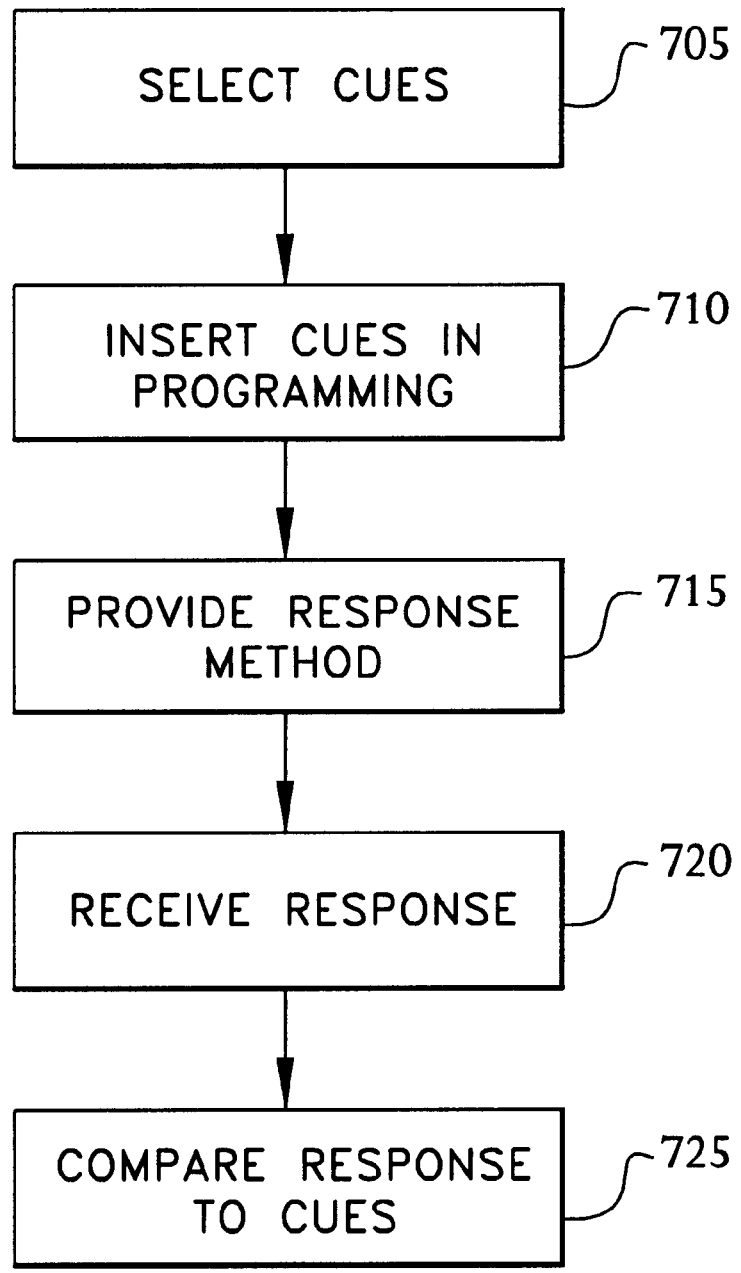
FIG. 7 is a flow chart showing steps in a method according to the invention of verifying viewing of a program.

Referring to FIG. 7, the program software creates an identifier sequence of cues, as indicated by block 705. The cues may be numbers, letters or other indicia, such as colors, shapes, sounds or combinations thereof, unique to each viewer and each program. The sequence may be derived from such information as the viewer's ID number, such as the Social Security number or other unique record locator contained in the patient/viewer record database, the unique segment and/or program ID numbers or the content of clips or other portions of programming delivered to the viewer. Regardless of the method employed, a unique key sequence, or unique sequence of cues, which may be alphanumeric or comprise a series of images, icons, colors or sonic cues, is created. This sequence is unique to the customized video program. The elements of the sequence are recorded within the program, as indicated by block 710. The cue are preferably spread throughout the temporal sequence of the viewing experience one or more cues at a time. By way of example, numbers in the sequence may be superimposed over picture elements using character generation and keying. The picture sequences which underlie these characters may, or may not address the superimposed characters/numerals. In the case of audio cues, it is of course more likely that a specific sequence, such as a talking head, would be employed to communicate the cue. A special case of the cue is the use of actual questions, usually relating to viewer comprehension of the presented material and having multiple choice responses.

As indicated by block 715, the viewer is provided with a method for response. The response method includes suitable method to record these numbers, characters, colors, shapes or other cues contained within the sequence. For viewers who are receiving the programming online through a modem or Internet link, this might be a window which remains open and active during the playing of the video sequence, or which becomes open and active upon the presentation of the appropriate superimposed strings, which allows the viewer the opportunity to record that sequence. For videotapes delivered to the viewer, a card may be delivered together with the videotape. The card may contain boxes to be checked, blanks to be filled in, or choices of opaque coverings to be removed. Suitable instructions will be provided in the video for the viewer to scratch off or mark the card in an appropriate place.

In the case of scratch-off cards, or other pre-prepared cards, it is significant that colors and/or shapes might be employed rather than known characters, or as elements in known characters, like the commonly employed segments of characters used in LED displays. Some action is required of the viewer to cause these characters/signs to be recorded/ transferred to the recording area. These cards might bear sponsorship or advertising data and this data might also generate or contain further fields. These cards, or on-line components might come from a third-party source. For instance the on-line window might be generated for, or by, an advertiser or vendor. A paper-based recording space which might be contained in a booklet, magazine, newspaper or as part of the packaging itself, may also be generated by or for an advertiser or vendor. Such a recording space may be a peel-off videocassette label or a peel-off, tear-off, scratch-off, or stick-on component of the videotape packaging or its electronic analog. This component might also contain one or more other characters, colors, icons or strings which might be included in the final string, or used separately. This component might also be custom-generated as part of the custom packaging. For instance, the sequence ABC-might already occupy a place in the sequence-recording fields such as ABC-xxx-xxx-xxx. The ABC-might be visible or might require manual intervention or problem solving to reveal. This problem solving might be related to the material presented on the video. For example, a scratch-off grid of multiple choice questions, or an on-line emulation of such a grid, presented by the programming or packaging itself might yield a unique sequence of characters or signs.

The final uses of this character string are manifold, but the overarching intention is to provide a motivational arena for the recording of this verification data. The verification data, unless used in an on-line environment where the respondent is known to the system, usually contains fixed identifying data used to confirm the identity of either the viewer/ respondent or the specific program viewed. It may also include, or consist solely of, data strings generated in response to queries. It may further include gaming fields and or third-party sponsored information.

In the case of traditional videotaped or other passively consumed media, the response data can be collected swiftly by 800-number, or standard toll-line, call-in to an automated collection system, which has been programmed in a suitable manner to collect response data. The response data can also be collected by mail-in and even correlation with sealed-envelope or other hidden message systems such as peel-open and scratch off answer fields which provide interim instructions. For viewers with suitable computer equipment, the response data can be returned by electronic mail. The receipt of responses is indicated by box 720. The end result though is, at minimum, the verification of active viewing of the temporal stream of information. The responses are compared to cues and expected responses, as indicated by block 725. At maximum, the information is also capable of verifying time of viewing, comprehension of content, attitudes regarding content (by asking for reactions in some or all of the fields), as well as motivating viewers with the possibility of prizes, secrets, entry into further lotteries or drawings, or other perceived rewards. The information can be used to instruct viewers to view the material again, make calls or other responses to the system, view or read additional, supporting or further material. All of this, significantly, can be done while maintaining complete viewer privacy. It may also be important that some of the feedback can be local to the viewer, while other portions of the response-strings may involve system-collection of responses.

Techniques may be used for distinguishing between incorrect responses resulting from a failure to view or comprehend the programming and an error in completing a response card. Techniques may also be used for identifying the most likely error in optical character recognition review of responses. The sequence of numbers, letters, or other visual or audio cues which is generated for and inserted in the programming is also used to generate computer-readable printed information, such as bar code, corresponding uniquely to that sequence. Customized codes may be developed to correspond to cues other than alphanumeric characters. The printed information is applied to a return card supplied with a videocassette on which the programming has been recorded. The printed information may be encoded, by altering the order of codes or including additional codes or other known techniques, for security purposes. Correct answers to question fields may be embedded in the bar coded string.

Acceptable tolerances for error within which the respondent will be deemed to have viewed and/or adequately comprehended the programming may be determined for each position of the character string. Numerous considerations may be used in determining these tolerances. Exemplary considerations are the following: (1) the first position of the string is prone to a heightened incidence of general user error; (2) fields which call for the answering of questions or scratching off of a layer of obscuring material are subject to a heightened incidence of general user error; (3) for positions known to include only a limited number of possible responses, statistical weighting can be employed to assign unclear responses into one of the known responses, e.g., if the possible responses are to write out one of the capital letters A, B, C and D, and an OCR program reads a response as the numeral 0, the response will be assigned as the letter D; (4) in a system employing scratching off of selected areas on the face of a response card, columns which contain more than one removed field where one field is correct and not more than two fields are removed. A weighted tolerance system may also employ other strategies. For example, a parity field may be derived from a modulo-cycling of the total character string, where the base number of the modulus might be the number of total possible characters potentially employed in a single field of the string. By way of further example, a system may be used which causes an known and repeatable limitation to be placed on the possible use of a given character derived from the earlier or other character in the string. The source of such a check character is from within the printed information, whereas the checked characters are from the handwritten or scratch-off fields. For example, the presence of an even number in the first position of a string might dictate the use of an odd number in the second field. Alternatively, a template could be created which would dynamically or in a predetermined manner limit the possible characters or other cues which could be employed in each position of the generated string. This data can be used to optimize the OCR function of each position of the response string, as well as to dynamically shift the error tolerance on a position-by-position basis.

By creating a master parity character and a known pattern in the string of characters, it is many times more probable that a single incorrectly read character can be isolated by the logical cross-reference of the two strategies set forth above. For example, if the parity check is incorrect by one value, and the fourth position of the string should be an odd number, but is read as the numeral 8, it is likely that the fourth field contains the numeral 8 if it is also true that the fourth field cannot by design contain an even number. When such techniques are combined with dynamically weighted general error correction, the scheme becomes tolerant of user inaccuracies and OCR errors.

For the presentation of video-superimposed characters, a static template could also be used which matches an accompanying printed template. Alternatively, video-generated characters could be derived dynamically from the character sequence used to identify the viewer. In this scenario, multiple-choice questions asked of the viewer would be presented on screen as would be the appropriate multiple-choice answers, but the characters used to identify the answers would be dynamically generated in response to the viewer or programming identification sequence. For example, if an algorithm generated the output X, then the characters A, B, C and D would be generated next to four multiple-choice answers appearing on screen. If the algorithm generated an output of Y, the answers would be assigned the numerals 1, 2, 3 and 4. Such a technique has the advantage of allowing the video assets containing test materials to remain mutable while responding dynamically to the needs of the error-correcting/checking system. It will be understood that the foregoing techniques may be employed with any visual, sonic or other cue.

Various points of the systems that are believed by the inventor will now be emphasized. However, the enumeration of certain features believed to be novel should not be construed as implying that other features are not novel.

The system provides for a database of assets which must be arranged temporally in order to be used, but which does not dictate the temporal organization. Rather, the audio and video assets in the database are characterized by such parameters as content, aesthetic features, and suitability to viewers with certain demographic or psychographic characteristics. The user can select assets through a suitable query without attention to temporal organization. The organization of assets contrasts with the organization of assets in such fields as video games. In a video game, the permitted temporal orders of the assets are predetermined by a strict branching system. Such a branching system defines precisely which asset may be permitted to follow which under all possible circumstances. The database of the present system may be termed amorphous, in contrast to the rigid organization of a database having a branching system. The general principle can be extended to other types of assets that require temporal organization in order to be used. For example, a database can be constructed for use with still photographs to be arranged into a program with an audio track. Interactive assets, such as two-dimensional or three-dimensional models and graphical user interfaces can also be catalogued in a database of this type. The present also contrasts to traditional databases in that it mines non-linear assets for presentation in a linear manner, the linear manner not being contained within the assets. The use of a moderation layer that limits the assets responsive to the query that are actually presented to the user contrasts with traditional database organization, in which all items responsive to a query are presented to the user.

The system also provides for the automatic creation of new programming, uniquely configured to the requirements of the viewer, but which may be viewed passively. In contrast, in such fields of video games, while the creation of unique programming occurs, the viewer must interact with the system in order to create the programming.

The system is also capable of arranging assets in an order, and creating transitions between assets, to create a concatenated stream of audiovisual programming that has transitions that appear to the viewer to have been edited by a human editor. Even without temporal order, the assets contain sufficient transition information, and the system contains default transition choices, to permit assembly of programming with fluid transitions without the intervention of a human editor. Numerous methods are available for ordering the assets in such a program. As discussed, assets may be ordered by using a template that imposes sequential requirements on the assets, an expert system, a truth table, or a human editor may decide the order of the assets. The attributes of the assets impose certain limitations on the ordering of the assets. For example, it may not be possible for aesthetic reasons to place a certain clip immediately before or after a certain other clip.

The individual assets may have demographic characteristics. For example, an audiovisual clip may feature actors of a particular ethnic group, geographic origin, age, or other demographic characteristic. As a result, the assets may be selected based on demographic search criteria.

The system may permit, in an on-line environment, switching between a predetermined program and interactive video. For example, the system may provide delivery of a predetermined audiovisual program so long as the viewer does not seek to interact with the system, e.g., by positioning a mouse pointer on the screen and clicking. At this point, the system may select assets that are appropriate to the particular information that the viewer appears to be seeking based on the information on the screen at the time. The system will then generate suitable transitions and add those assets to the programming. For example, the program may be a tour of a three-dimensional model of the heart. When the user moves a pointer or mouse to a particular portion of the screen, and clicks on the screen, the system may select, for example, assets incorporating more detailed information on certain portions of the heart corresponding to material on the portion of the screen where the mouse was located when clicked. The system applies suitable transitions to the assets and incorporates these assets into the programming interactively in response to mouse clicks or other suitable input from the viewer. This interactive generation of programming for passive viewing contrasts with existing systems that include a predetermined loop if the viewer does not provide inputs.

The system may also be employed in an interactive system that leads the viewer to select a desired sequence. The system may, for example, provide more interesting visual data in areas of the screen that lead to the selection of material that the viewer should see, or provide smooth transitions from audiovisual assets incorporated in the program as a result of viewer input to audiovisual assets incorporated in the program to achieve a predetermined purpose, e.g., to convey certain information to the viewer.

While specific embodiments of the invention have been described in detail, it will be appreciated by those skilled in the art that various modifications and alternatives to those details could be developed in light of the overall teachings of the disclosure. Accordingly, the particular arrangements of the system and method disclosed are meant to be illustrative only and not limiting to the scope of the invention, which is to be given the full breadth of the following claims, and any and all embodiments thereof.

What is claimed is:

1. A method of creating media programming, comprising the steps of:

maintaining a database containing selected information about each of a plurality of media elements;

automatically selecting a plurality of said media elements in response to a request for media programming, and automatically selecting a temporal organization for said selected media elements, said temporal organization not being dictated by said selected information; and assembling said media elements into media programming.

2. The method of claim 1, wherein said media elements are audiovisual clips, and said media programming is an audiovisual program.

3. The method of claim 1, wherein said media elements are still photographs, and said media programming comprises a series of said still photographs.

4. The method of claim 1, wherein said selected information comprises content information relating to said media assets.

5. The method of claim 1, wherein said selected information comprises a plurality of tags associated with each of said media elements, at least one of said tags being a content tag containing information relating to content of said media element, and at least one of said tags being a control tag containing information other than content information.

6. The method of claim 5, wherein said media element in an audiovisual clip, and at least one of said control tags contains information indicating permitted transition points in said audiovisual clip.

7. The method of claim 6, wherein at least one of said control tags contains a luminance range for a portion of said audiovisual clip.

8. The method of claim 5, wherein said step of selecting further comprises selecting two elements based on said request, selecting a temporal order for said two elements, and determining based on information in said control tags whether said two elements may be assembled in the selected temporal order, and, if not, deselecting at least one of said two elements.

9. The method of claim 5, wherein said step of selecting further comprises selecting two elements based on said request, selecting a temporal order for said two elements, and selecting transitions for said two elements based on transition information associated with each of said elements and transition rules.

10. The method of claim 1, further comprising the step of obtaining demographic information concerning an intended view of a the programming prior to said step of selecting, and employing said demographic information in said step of selecting.

11. A system of creating media programming from a library of media assets, comprising:

a database containing selected information about each of said media assets;

selection means for automatically selecting a plurality of said media assets in response to a request for media programming, and for automatically selecting a temporal organization for said selected media assets, said temporal organization not being dictated by said selected information; and assembling means for assembling said media elements into media programming.

12. The system of claim 11, wherein said media elements are audiovisual clips, and said media programming is an audiovisual program.

13. The system of claim 12, wherein said media elements are still photographs, and said media programming comprises a series of said still photographs.

14. The system of claim 11, wherein said selected information comprises content information relating to said media assets.

15. The system of claim 11, wherein said selected information comprises a plurality of tags associated with each of said media elements, at least one of said tags being a content tag containing information relating to content of said media element, and at least one of said tags being a control tag containing information other than content information.

16. The system of claim 15, wherein said media element is an audiovisual clip, and at least one of said control tags contains information indicating permitted transition points in said audiovisual clip.

17. The system of claim 16, wherein at least one of said control tags contains a luminance range for a portion of said audiovisual clip.

18. The system of claim 15, wherein said selecting means further comprises means for selecting two elements based on said request, means for selecting a temporal order for said two selected elements, means for determining based on information in said control tags whether said two elements may be assembled in the selected temporal order, means for deselecting at least one of said two elements if said two elements are not permitted to be assembled in the selected temporal order.

19. The system of claim 15, wherein said selecting means further comprises means for selecting two elements based on said request, for selecting a temporal order for said two elements, and for selecting transitions for said two elements based on transition information associated with each of said elements and transition rules.

20. The system of claim 11, further comprising means for obtaining demographic information concerning an intended viewer of the programming, said selecting means being adapted to employ said demographic information.

21. The system of claim 11, wherein said selection means comprises means for selecting fewer than all of said media elements responsive to said request.

22. The system of claim 11, wherein said selection means prevents a user from selecting or ordering said media elements.

23. A method for verifying viewing and comprehension of a unique media program, comprising the steps of:

providing in a unique media program a unique sequence of cues; and receiving from a viewer of said unique media program information relative to said cues; and comparing said received information to said sequence of cues.

24. The method of claim 23, wherein said step of providing a unique sequence of cues comprises providing a unique sequence of visual cues in an audiovisual program.

25. The method of claim 23, wherein said cues comprise alphanumeric information.

26. The method of claim 23, wherein said visual cues comprise icons.

27. The method of claim 23, further comprising the step of providing means for a viewer to transmit said information.

28. The method of claim 27, wherein said step of providing comprises incorporating with programming media a printed document to be completed and returned by a viewer.

29. The method of claim 23, wherein said step of receiving information comprises receiving information via telephone communications.

30. A method of creating audiovisual programming from a plurality of stored audiovisual media elements, comprising the steps of:

automatically selecting from a database containing information concerning said audiovisual media elements a plurality of said audiovisual media elements and automatically designating a temporal sequence for said selected audiovisual media elements, selecting automatically transitions for each of said audiovisual media elements.

31. The method of claim 30, wherein said step of automatically selecting transitions comprises selecting transitions independently for a video portion of said element and for an audio portion of said element.

32. The method of claim 30, wherein said transitions are selected based on information relating to permitted transitions associated with each of said elements.

33. The method of claim 30, wherein said transitions comprise fade out of a video portion of said element.

34. The method of claim 30, wherein said information comprises a range of permitted transition points at the beginning and end of a plurality of said elements.

35. The method of claim 34, wherein said information comprises an earliest permitted transition point, a default transition point, and a latest permitted transition point.

36. A system for creating audiovisual programming from a plurality of stored audiovisual media elements, comprising:

means for automatically selecting from a database containing information concerning said audiovisual media elements a plurality of said audiovisual media elements and automatically designating a temporal sequence for said selected audiovisual media elements, and means for selecting automatically transitions for each of said audiovisual media elements.

37. The system of claim 36, wherein said means for automatically selecting transitions comprises means for selecting transitions independently for a video portion of said element and for an audio portion of said element.

38. The system of claim 36, wherein said transitions are selected based on information relating to permitted transitions associated with each of said elements.

39. The system of claim 36, wherein said transitions comprise fade out of a video portion of said element.

40. The system of claim 36, wherein said information comprises a range of permitted transition points at the beginning and end of a plurality of said elements.

41. The system of claim 40, wherein said information comprises an earliest permitted transition point, a default transition point, and a latest permitted transition point.

\* \* \* \* \*